United States Patent [19]

Österdahl

[11] Patent Number: 5,634,915
[45] Date of Patent: Jun. 3, 1997

[54] METHOD FOR THE MANUFACTURING OF AN ABSORBENT STRUCTURE AND AN ABSORBENT ARTICLE COMPRISING AN ABSORBENT STRUCTURE MANUFACTURED ACCORDING TO THIS METHOD

[75] Inventor: Eje Österdahl, Frölunda, Sweden

[73] Assignee: Mölnlycke AB, Goteborg, Sweden

[21] Appl. No.: 442,155

[22] Filed: May 16, 1995

[30] Foreign Application Priority Data

Nov. 17, 1992 [SE] Sweden ........................ 9203446

[51] Int. Cl.$^6$ .................................. A61F 13/15
[52] U.S. Cl. ................. 604/379; 604/380; 604/367; 604/368; 604/374; 604/375
[58] Field of Search .................. 604/374, 375, 604/378, 379, 380, 384, 367, 368, 369

[56] References Cited

U.S. PATENT DOCUMENTS

| | | |
|---|---|---|
| 4,507,122 | 3/1985 | Levesque . |
| 4,590,114 | 5/1986 | Holtman ..................... 428/171 |
| 4,610,678 | 9/1986 | Wiesman et al. . |
| 4,898,642 | 2/1990 | Moore et al. ................ 604/375 |
| 5,009,650 | 4/1991 | Bernardin ................... 604/374 |
| 5,188,624 | 2/1993 | Young, Sr. et al. ............ 604/378 |

FOREIGN PATENT DOCUMENTS

| | | |
|---|---|---|
| 0202472A1 | 11/1986 | European Pat. Off. . |
| 0251675A2 | 1/1988 | European Pat. Off. . |
| 0255654A1 | 2/1988 | European Pat. Off. . |
| 0360472A2 | 3/1990 | European Pat. Off. . |
| 0523744A1 | 1/1993 | European Pat. Off. . |
| 468 744 | 3/1993 | Sweden . |
| 2140471 | 11/1984 | United Kingdom . |
| 9005808 | 5/1990 | WIPO . |
| WO90/05808 | 5/1990 | WIPO . |
| 9111162 | 8/1991 | WIPO . |

*Primary Examiner*—John G. Weiss
*Assistant Examiner*—David J. Cho
*Attorney, Agent, or Firm*—Burns, Doane, Swecker & Mathis LLP

[57] ABSTRACT

A method of producing an absorbent structure in an absorbent article includes the steps of compressing an air laid web of cellulose fibers into a dry-formed sheet having a first density of between 0.2–1.0 g/cm$^2$ and mechanically softening the compressed sheet by a noncutting method to a second density, which is lower than the first density, whereby the sheet is delaminated so as to form a plurality of partially separated thin fiber layers, each of which layers exhibits a density which corresponds to the first density.

30 Claims, 6 Drawing Sheets

METHOD FOR THE MANUFACTURING OF AN ABSORBENT STRUCTURE AND AN ABSORBENT ARTICLE COMPRISING AN ABSORBENT STRUCTURE MANUFACTURED ACCORDING TO THIS METHOD

CROSS-REFERENCE TO RELATED APPLICATIONS

This application is related to the international application PCT SE93/00975, which designated the United States.

BACKGROUND

1. Field of the Invention

The present invention relates to a method for manufacturing an absorbent structure in an absorbent article, such as a sanitary napkin, a tampon, a panty protector, an incontinence guard, a diaper, a bed protector, a wound or sore dressing, a saliva absorbent, and like articles. The invention also relates to an article manufactured according to the method.

2. Discussion of Related Art

Many types of absorbent articles of this kind are known to the art. The absorbent bodies of such articles are typically produced by dry-defibering and fluffing cellulose pulp in roll, bale or sheet form for instance, to form a pulp mat, sometimes admixed with so-called superabsorbents in the pulp mat, these superabsorbents being polymers which are capable of absorbing many times their own weight of water or body fluid.

The pulp body is often compressed so as to enhance its fluid wicking ability and also in order to reduce the bulk of the pulp body and therewith obtain an article which is as compact as possible.

The absorbent body may also include other constituents, for instance constituents which will improve its fluid aquisition properties or its fluid-wicking properties, or to increase its coherent strength, i.e. its coherency, and its ability to withstand deformation in use.

One serious drawback with products of this nature is found in the total absorption capacity of the articles and also in the fact that the articles will often leak long before their total absorption capacity has been fully utilized. Among other things, this is because the body fluid discharged by the wearer is unable to penetrate into the absorption material and to spread to hitherto unused areas of the article quickly enough, but instead leaks from the sides of the sanitary napkin, diaper or incontinence guard. The ability of the materials used in the article to disperse the absorbed fluid throughout the entire absorbent body is thus highly important.

Another problem resides in so-called rewetting, i.e. the transference of body fluid that has already been absorbed back into contact with the wearer's skin as a result of external forces, for instance when the wearer sits down. It is generally desired that the surface of the article that lies proximal to the wearer will remain as dry as possible.

Another desideratum with regard to the majority of hygiene products is that the article shall be thin and soft, so that it can be worn as discretely as possible. For some purposes the compressed absorbent body of the absorbent article is softened to achieve the desired softness. One method to soften an absorbent sheet is described in European Patent Application EP 0 360 472, where the compressed absorbent material is worked between partially cutting rollers and thereby gaining softness. This method however leads among other things to decreased strength in the softened material.

It is known from International Patent Application WO 90/05808 to produce a pulp web which is later defibred, so-called dry-formed roll pulp. Flash-dried fibres of paper pulp, which may consist of thermomechanical pulp, chemi-thermomechanical pulp CTMP, or chemical paper pulp, sulphite or sulphate pulp with a dry solids content of about 80%, is delivered by means of an air stream in a controlled flow to a forming head arranged above a forming wire and there formed into a web that has a per unit area weight of 300–1500 g/m2 and a density of 550–1000 kg/m3. Air is sucked away through a suction box placed beneath the wire. The moisture content in the process shall be 5–30%.

The web is pre-pressed to a density of 550–1000 kg/m3 in order to slightly reduce the bulk of the web, prior to the final pressing stage. The pressed web thus has a mechanical strength which enables it to be rolled-up or handled in sheet form for storage and transportation purposes. The web can be readily defibred and is intended to be convened into fluff for use in the manufacture of absorbent bodies or pads for diapers, sanitary napkins and like articles.

SUMMARY AND OBJECTS

An object of the present invention is to provide in an absorbent article of the aforedescribed kind an absorbent structure which exhibits extremely good absorption properties, both with respect to its ability to quickly take up fluid and also its ability to spread the fluid throughout the material. The material will preferably have low rewetting tendencies and will also be capable of being made very thin. It is also desirable, among other things from the aspect of flexibility, to be able to use both dry-formed roll pulp and conventional fluff pulp as a starting material and achieve equivalent article properties.

This object is achieved in accordance with the present invention by, in immediate conjunction with the manufacture of the absorbent article, compressing an air-laid web of cellulose fibres, subsequent to conventional defibering and fluffing of the web, to a dry-formed sheet having a weight per unit area of between 30–2000 g/m2 and a first density of between 0.2–1 g/cm3, and then softening the sheet mechanically to a second density which is lower than the original density and therewith delaminating the sheet, so that the resultant structure forms a plurality of partially separated thin fibre layers which in themselves have a density corresponding to the first density.

BRIEF DESCRIPTION OF THE DRAWINGS

The invention will now be described in more detail with reference to a number of exemplifying embodiments thereof and also with reference to the accompanying drawings, in which.

DETAILED DESCRIPTION OF PREFERRED EMBODIMENTS

Figure 1:
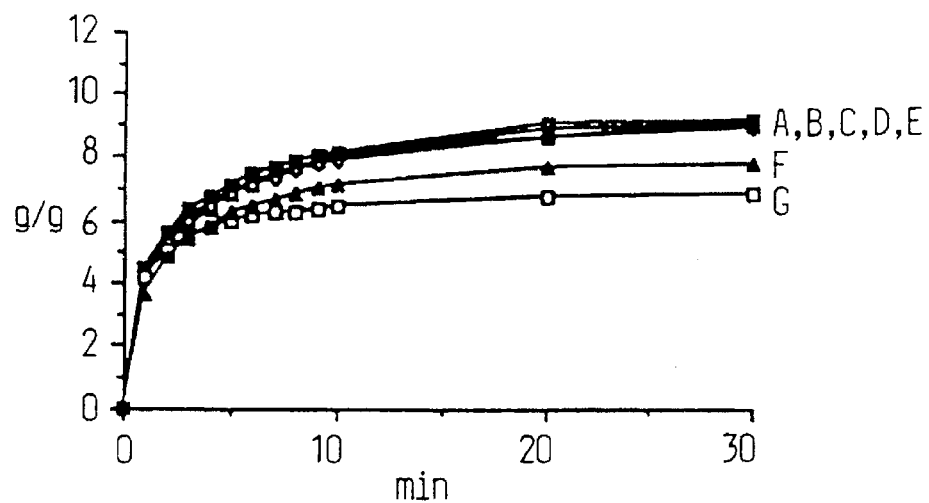
FIG. 1 illustrates the absorption properties of a dry-formed CTMP-material subsequent to being worked between rolls at different roll spacings. Conventionally formed and compressed pulp mats of CTMP-pulp and chemical pulp respectively were used as references.

Important properties of a material used in the manufacture of a hygiene article are its absorbent capacity, absorption rate, fluid-dispersion capacity, drainage capacity, fluid retention capacity, rewetting tendency, softness and smoothness.

The fluids concerned are urine, menstruation blood, blood, fluid matter from wounds and sores, rinsing fluid and saliva.

An object of the present invention is to provide in an absorbent article, such as a sanitary napkin, tampon, panty protector, incontinence guard, diaper, bed protector, wound dressings, saliva absorbents and the like, an absorbent structure which exhibits highly effective absorption properties, both with regard to its fluid-aquisition rate and in its ability to disperse the fluid throughout the material. The material will also preferably have low rewetting tendencies and capable of being made very thin.

Untreated, dry-formed roll pulp has very good absorption properties, fluid-wicking properties and swelling properties, and it has been found possible to use this material as an absorbent material directly in hygiene articles without defibering the material. In the case of certain absorbent articles, it is beneficial to soften the material in some way or another. A method of softening the material mechanically is described below. Conventional fluff pulp does not normally possess these properties.

It is desirable, among other things from the aspect of flexibility, to be able to use both dry-formed roll pulp and conventional fluff pulp as starting materials and, nevertheless, achieve the same good properties as those achieved with a product manufactured from dry-formed roll pulp.

This is achieved with the aid of the present invention, by compressing an air-laid web of cellulose fibres in immediate conjunction with the manufacture of said absorbent article and subsequent to conventional defibration and fluffing, into a dry-formed sheet having a pertinent area of between 30–2000 g/m2 and a first density of between 0.2–1.0 g/cm3, and softening the sheet mechanically to a second density which is lower than the first density and herewith delaminate the sheet so that the structure forms a plurality of partially separated thin fibre layers which in themselves have a density which corresponds to the first density.

When practicing the present invention using conventional defibration and fluffing, there may be used different kinds of pulp, for instance a wet-formed or dry-formed product manufactured from mechanical pulp or chemi-thermomechanical pulp (CTMP) or a corresponding product manufactured from sulphite or sulphate pulp, so-called chemical cellulose pulp. Cellulose fibres which have been stiffened chemically may also be used.

In the case of certain absorbent articles, it is suitable to soften the material used in some way or another. A method of softening the material mechanically is described below.

Cellulose pulp fibres have a so-called curl value which defines the degree of crookedness of the fibre. Curl value can be measured according to the method described by B. D. Jordan, N. G. Nguyen in Papper och Trä, 4/1986, page 313.

In one embodiment, the chemi-thermomechanical pulp fibers have a curl value of between 0.20 and 0.40.

Softening of the Material

The material can be given a softness which renders the material highly suitable for use as an absorbent material in the majority of hygiene articles, by working dry-formed roll pulp between rolls, for instance between corrugated rolls. The material can be brought to different degrees of softness for different product applications, by working the material between different types of rolls, different patterns in the rolls and at different roll spacings.

Dry-formed roll pulp exhibits very good product properties when softened in this way, and the earlier mentioned good absorption properties are not influenced by the softening process to any great extent.

Figure 15:
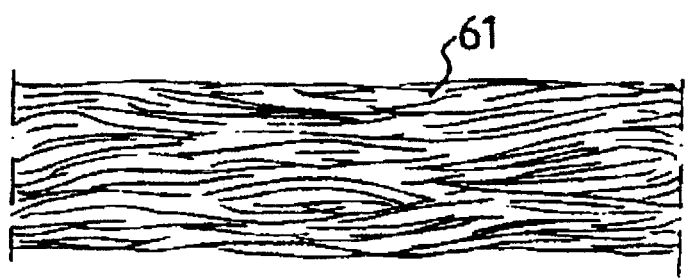
FIG. 15 illustrates the structure of a cross section of the material in unsoftened condition.
Figure 16:
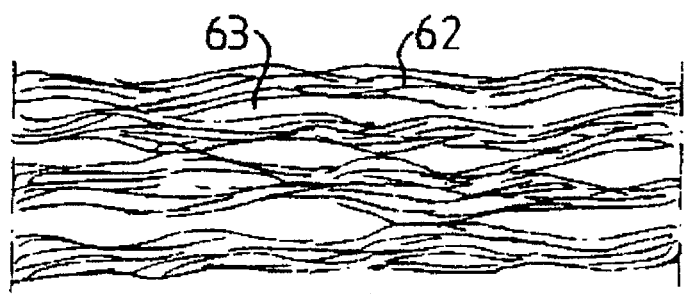
FIG. 16 illustrates the structure of a cross section of the material in softened condition.

The material is delaminated in the softening process as illustrated in FIGS. 15 and 16. The unsoftened material has normally an even high density throughout the whole the thickness of the material (61). As a result of the softening process the material is delaminated so as to form a plurality of partially separated (63), thin fibre layers (62). Softening and delamination of the material reduces its total density to some extent, although the original density is essentially retained in each individual layer. Because a very high density is retained in the individual layers, the good fluid wicking properties of the material are retained despite the increase in bulk obtained in conjunction with the softening process. The total bulk is increased by up to 300%, normally 1–100%, as a result of the softening process, depending on the method used and the extent to which the material is softened.

It will be understood that the aforesaid material softening method is given solely by way of example and that corresponding results can be achieved with the aid of other methods. For instance, the material could eventually be softened by means of ultrasonic energy, microwaves, by moisturizing the material or with the aid of chemical additives.

Investigation of Material Properties

The test equipment described below was used to evaluate the absorption properties.

Method 1. Absorption Properties Up an Inclined Plane

A rectangular test body was punched from the material and a line was drawn transversely across the test body at a point 11 cm from one short end of the body. A fluid container was placed adjacent laboratory scales and both the scales and the container were adjusted to a horizontal position. A plexiglass plate was placed on the scales at a 30 slope, with one free edge of the plate extending slightly down into the container. A line had been drawn transversely across the plate at a point 11 cm from the lower edge of said plate. Test fluid (0.9% NaCl-solution) was poured into the container, until 20 mm of the plexiglass plate was located beneath the surface of the liquid. The test body was secured on the plexiglass plate so that the line drawn on the test body coincided with the line drawn on the plate while, at the same time, folding away the lower part of the test body so as to prevent it from coming into contact with the test liquid. A clock was started at the same time as the test body was laid onto the plate, with the test body extended down into the solution to the same extent as the plate. The increase in weight of the test body with time was recorded.

Method 2. Measuring Absorption Capacity and Degree of Utilization

A test product was secured in a fixture. Test fluid (0.9% NaCl-solution) was delivered to the wetting point of the product over a period of 60 minutes at the rate at which the fluid was absorbed. The amount of fluid absorbed was measured continuously and the total mount of fluid absorbed by the product constitutes the utilized absorption capacity of the test product. The test product was then placed in a fluid bath, in which it had the maximum opportunity of absorbing test fluid. The test product was then again weighed and the total absorption capacity calculated. The degree of utilization is constituted by the quotient between the utilized absorption capacity of the test product and the total absorption capacity.

Method 3. Determining Rewetting, Fluid Wicking and Aquisition Time

Four batches of sample fluid (0.9% NaCl-solution), each comprising 28 ml, were delivered at 20-minute intervals. The time measurement was continued until all fluid had been absorbed. The extent to which the fluid had dispersed in the diaper was noted after each batch. Subsequent to delivering the last batch of fluid, filter paper was placed over the wetting point and loaded with a weight of 1.1 kg for 15 seconds. The filter paper was weighed both before and after applying the load and rewetting was recorded.

Method 4. Determining Rewetting

A diaper intended for a given child weight range was weighed and then placed on a flat support surface. An adapted quantity of test fluid (0.9% NaCl-solution, 1.00 ml for a diaper intended for a child weight range of 7–15 kg) was delivered to the wetting point of the diaper. A further 100 ml of fluid was delivered after 20 minutes. When all fluid had been absorbed, a filter paper was placed over the wetting point and loaded with a weight of 1.1 kg for 15 seconds. The filter paper was weighed both before and after applying the load and the result was recorded as a first rewetting instance. After a further 20 minutes, another 100 ml of fluid was delivered and when all fluid had been absorbed, the procedure was repeated with a fresh filter paper and the result recorded as a second rewetting instance.

Method 5. Determining Blood Absorption

A test body, 65×200 mm, was punched from the material. 5 ml test fluid (0.9% NaCl-solution) were delivered to the wetting point on the test body. Dispersion of the fluid was measured after about 30 minutes. A further 5 ml of test fluid (0.9% NaCl-solution) were then delivered to the wetting point and fluid dispersion was measured after about a further 30 minutes. Subsequent to the last delivery, eight filter papers were placed over the wetting point and loaded with a weight of 4.875 kg for 15 seconds. The filter papers were weighed both before and after applying the load and rewetting was recorded.

Test Results

Softening

With the intention of investigating how the material was affected at different softening roll spacings when softening the material, a material was tested under different softening conditions. For instance, in the case of a dry-formed CTMP-material having a weight per unit area of 900 g/m2 and a density of 0.63 g/cm3, a suitable roll spacing is 1.7–2.4 mm during the softening process. The material is not influenced to any great extent at roll spacings which lie within this range. FIG. 1 illustrates the absorption properties at different roll spacings. The results were determined in accordance with Method 1.

A Material according to the invention, roll spacing 1.7 mm.
B Material according to the invention, roll spacing 2.0 mm.
C Material according to the invention, roll spacing 2.4 mm.
D Material according to the invention, roll spacing 2.0 mm, softened twice.
E Material according to the invention, roll spacing 2.0 mm, softened four times.
F CTMP-pulp, density 0.125 g/cm3.
G Chemical sulphate pulp, density 0.125 g/cm3.

Absorption Properties of Absorbent Structures

Figure 2:
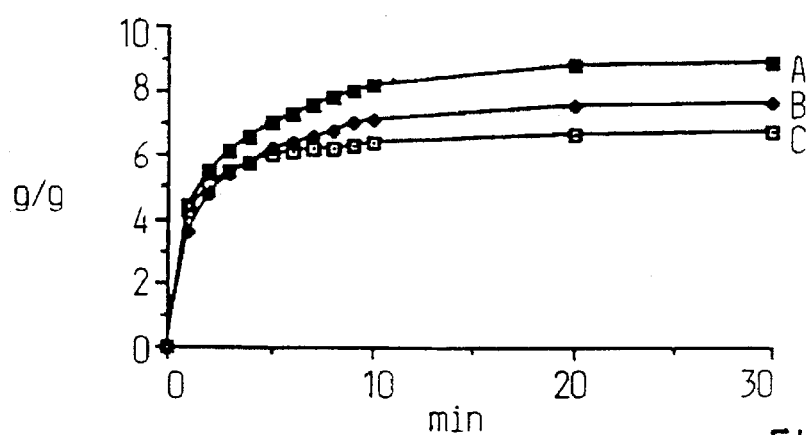
FIG. 2 illustrates the absorption properties of dry-formed CTMP-material subsequent to being softened. Conventionally formed and compressed mats comprised of CTMP-pulp and of chemical pulp respectively were used as references.

The absorption properties of an inventive CTMP-material having a weight per unit area of 900 g/m2 and a density of 0.63 g/cm3 compared with those of corresponding pulp cores produced from conventionally defibred and web-formed CTMP and corresponding chemical pulp are shown in FIG. 2. In the absence of superabsorbent material, the absorption capacity is about 9 g of fluid for each gram of absorbent material. The results were determined in accordance with Method 1.

A Material according to the invention.
B CTMP-pulp, density 0.125 g/cm3.
C Chemical sulphate pulp, density 0.125 g/cm3.

Product Properties of a Complete Absorbent Article

With the intention of studying other properties of complete absorbent articles, test products were prepared in the form of conventional children's diapers which comprised a T-shaped absorbent body (T-core) and a rectangular absorbent body (R-core), where the rectangular absorbent body in the test products was manufactured from a CTMP-material in accordance with the invention. In the conventional products, the T-shaped absorbent body (T-core) and the rectangular absorbent body (R-core) were comprised of conventional defibred CTMP and chemical pulp.

Measuring the Absorption Capacity

Figure 3:
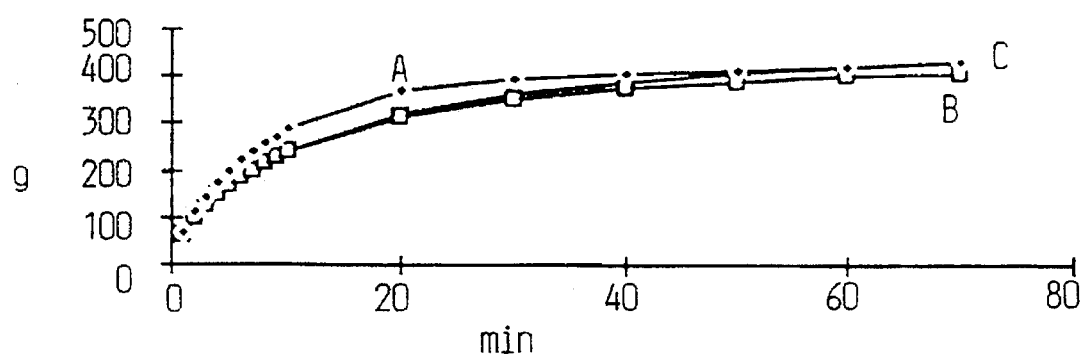
FIG. 3 illustrates the absorption properties of a complete absorbent article manufactured with dry-formed CTMP in the core. Conventionally manufactured products of corresponding compositions were used as references.

Products which comprised an inventive CTMP-material exhibited an absorption in grams which was equal to the reference products having corresponding pulp cores comprised of conventionally defibred and web-formed CTMP and chemical pulp. The results are set forth in FIG. 3. The results were determined in accordance with Method 2.

A Reference diaper Libero Girl.
B Reference diaper Libero Boy.
C Child diaper comprising inventive material.

Measuring Fluid Aquisition Time

Figure 4:
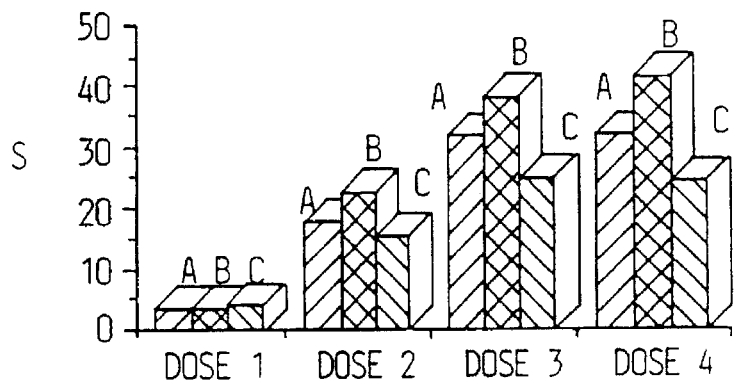
FIG. 4 illustrates the fluid aquisition time of a complete absorbent article manufactured with dry-formed CTMP in the core. Conventionally manufactured products of corresponding compositions were used as references.

Products in which the R-core comprised an inventive CTMP-material exhibited a shorter fluid aquisition time than the reference product. This implies that an inventive CTMP-material in the R-core is able to drain the T-core more effectively. The results are set forth in FIG. 4. The results were determined in accordance with Method 3.

A Reference diaper Libero Girl.
B Reference diaper Libero Boy.
C Child diaper comprising inventive material.

Measuring the Utilization of the Absorbent Body

Figure 5:
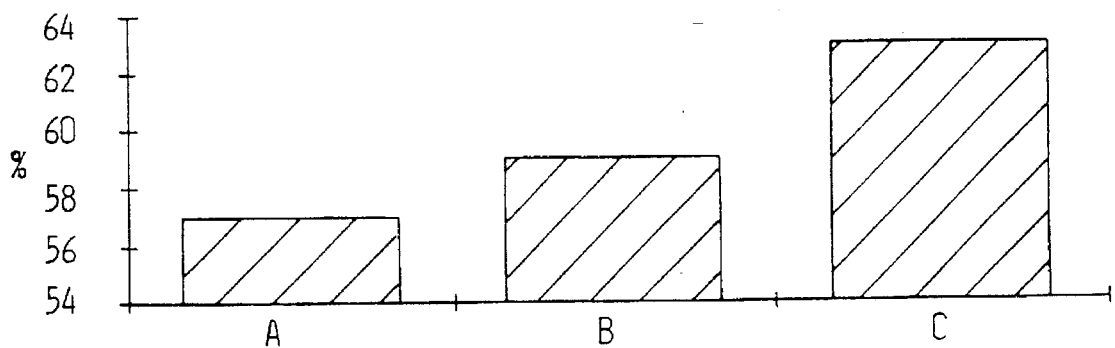
FIG. 5 illustrates the degree of utilization of a complete absorbent article manufactured with dry-formed CTMP in the core. Conventionally manufactured products of corresponding compositions were used as references.

A comparison between the degree of utilization of the absorbent body in an absorbent article which contained an inventive CTMP-material and a corresponding absorbent article which contained conventional CTMP and chemical pulp showed that the degree of utilization is about equal, although slightly on the plus side for an inventive CTMP-material. The results are set forth in FIG. 5. The results were determined in accordance with Method 2.

A Reference diaper Libero Girl.
B Reference diaper Libero Boy.
C Child diaper comprising inventive material.

Admixing Superabsorbent Material

Figure 6:
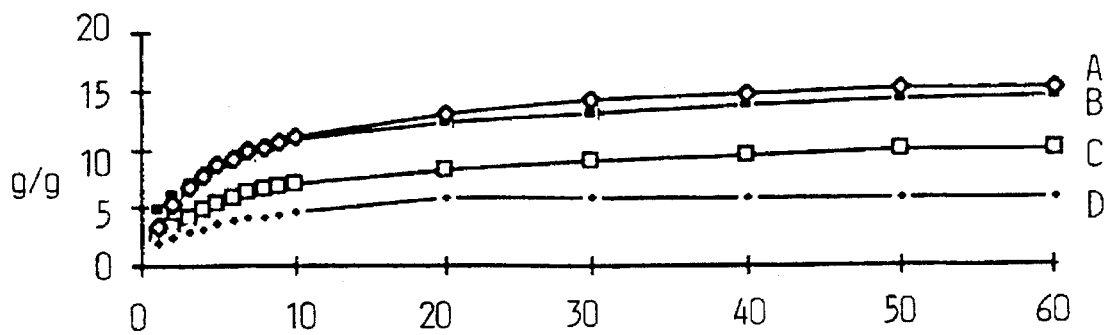
FIG. 6 illustrates the absorption properties of an absorbent structure produced from dry-formed CTMP, both with and without a superabsorbent admixture. Conventionally manufactured pulp cores both with and without a superabsorbent admixture were used as references.

The presence of superabsorbent material in an absorbent body will influence the absorption properties of the body. Superabsorbent material can be incorporated in the absorbent body in different ways, for instance it may be admixed with the body material, laid in layers in the body, or disposed in some other way. This admixture of superabsorbent material can be effected in conjunction with manufacturing the dry-formed material, although it may also be effected during some other part of the manufacturing process. The absorption properties were compared with an inventive CTMP-material to which no superabsorbent material had been added and also with corresponding pulp cores comprised of conventional defibred CTMP and chemical pulp. The results of this comparison are shown in FIG. 6. The results were determined in accordance with Method 1.

A Chemical sulphate pulp containing 30% superabsorbent and having a density of 0.125 g/cm3.
B Inventive material containing 30% superabsorbent.
C Reference diaper containing 30% superabsorbent.
D Inventive material containing no superabsorbent.

Measurements of Rewetting

Figure 7:
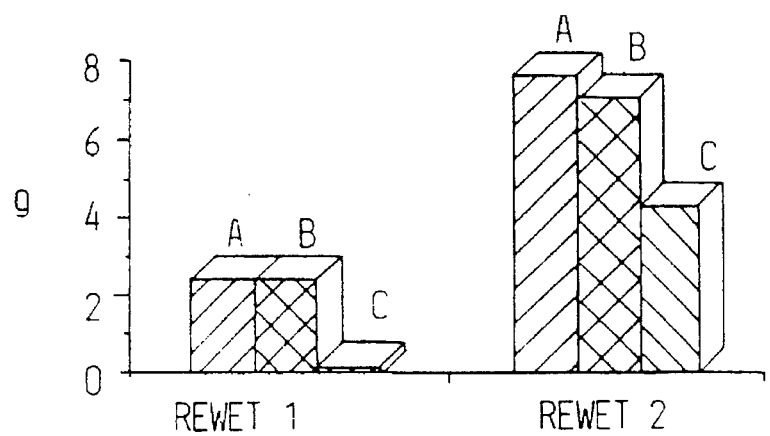
FIG. 7 illustrates the rewetting of a complete absorbent article produced with dry-formed CTMP in the core. Conventionally manufactured products of corresponding compositions were used as references.

Products which comprised an inventive CTMP-material in the R-core exhibited better rewetting values than the reference product. This also implies that an inventive CTMP-material in the R-core is able to drain the T-core more effectively. The results are set forth in FIG. 7. The results were determined in accordance with Method 4.

A Reference diaper Libero Girl.
B Reference diaper Libero Boy.
C Child diaper comprising inventive material.

Measurements of Rewetting, Specific for Blood Absorption

In the case of blood absorption, products comprising an inventive softened CTMP-material showed better rewetting values than non-softened products. The results also showed that in respect of blood absorption products which lacked superabsorbent material exhibited lower rewetting values than material which contained superabsorbent material. Material which lacks superabsorbent material also disperses blood much more effectively. The results are set forth in FIGS. 8 and 9. The reference products comprised two different products frequently found on the market. The results were determined in accordance with Method 5. The prerequisites for this effect are that at least one layer of the pulp mat is free from superabsorbent material, and this does not therefore exclude the presence of such material in other parts of the absorbent article.

Figure 8:
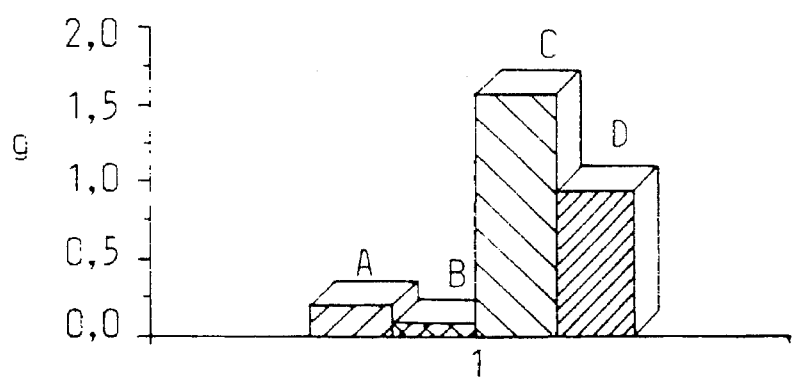
FIG. 8 illustrates the respective rewetting of an unsoftened and a softened absorbent structure which had absorbed blood and which was produced with dry-formed CTMP in the core, both with and without a superabsorbent admixture.

FIG. 8
A Inventive material 350 g/m2.
B Inventive material 350 g/m2, softened.
C Inventive material 350 g/m2+5% superabsorbent.
D Inventive material 350g/m2+5% superabsorbent, softened.

Figure 9:
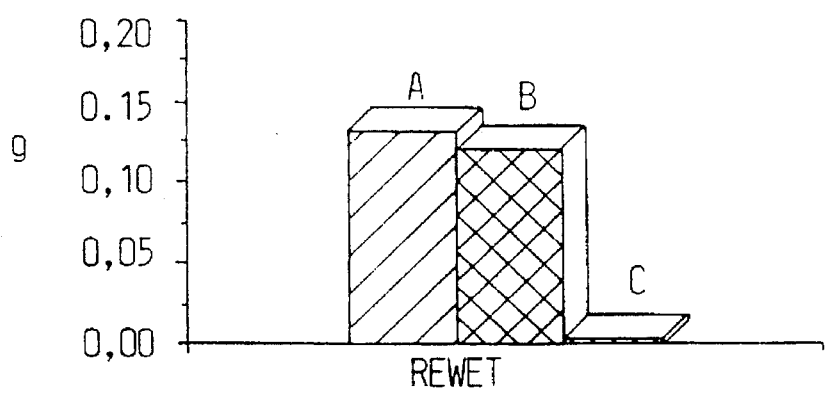
FIG. 9 illustrates the rewetting of a complete absorbent article which had absorbed blood and which was produced with dry-formed CTMP in the core. Conventionally manufactured products of corresponding composition were used as references.

FIG. 9
A Reference product 1.
B Reference product 2.
C Product containing inventive material.

Network Strength

Dry-formed roll pulp will normally have sufficient mat strength for the product applications intended here. If the network strength of certain product applications should be found insufficient, the network strength can be increased by reinforcing the structure in some suitable manner, by adding reinforcing fibres, binding fibres or binding agent to the cellulose fibre mixture. The network strength can also be increased by incorporating a reinforcing layer of, for instance, plastic, non-woven, net or threads in the absorbent structure, or by fastening a reinforcing layer or an outer sheet on one or both sides of the material.

Density and Weight per Unit Area

The softened pulp mat is still very thin, and consequently it is unnecessary in many cases to further compress the mat prior to its use in an absorbent article. A suitable density is 0.2–1.0 g/cm3, preferably 0.25–0.9 g/cm3 and most preferably 0.3–0.85 g/cm3. A suitable weight per unit area is between 30–2000 g/m2, preferably 50–1500 g/m2 and most preferably 100–1000 g/cm2. When calculating the density, the thickness of the material was measured with the aid of a Mitutoyo thickness meter.

Description of a First Exemplifying Embodiment

Figure 10:
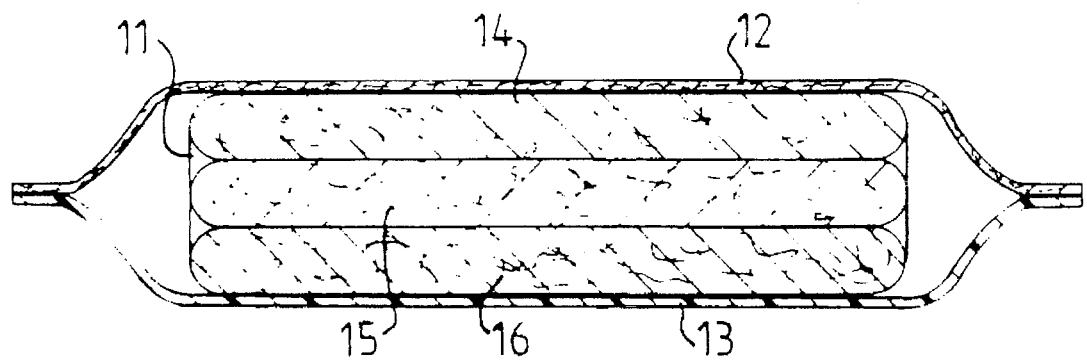
FIGS. 10–14 illustrate schematically the composition of various exemplifying embodiments of inventive absorbent articles.

FIG. 10 illustrates a diaper constructed in accordance with one embodiment of the invention. The diaper includes, in a conventional manner, an absorbent body 11 which is enclosed between a fluid-permeable top sheet 12, which conveniently comprises a soft non-woven material, a perforated plastic film or the like and which is intended to lie proximal to the wearer in use, and a fluid-impermeable bottom sheet 13. The sheets 12 and 13 have parts which extend beyond the absorbent body 11 and the sheets are joined together at these protruding parts. The bottom sheet 13 is comprised of a suitable plastic material, for instance polyethylene. It will be understood, however, that other known materials can be used for the top and bottom sheets, within the scope of the invention.

The absorbent body is comprised of two or more layers, an upper aquisition layer 14 and one or two lower wicking layers and storage layers 15 and 16. The inventive material can be used either as an aquisition layer 14, a wicking layer 15 or a storage layer 16 or as several of these layers. Those layers in which inventive material is not used can include types of other materials, for instance conventional cellulose fibre material.

The purpose of the aquisition layer 14 is to rapidly receive a given quantity of fluid. This fluid shall solely be held loosely in the fibre structure and quickly drained therefrom. The aquisition layer 14 is comprised of dry-formed material in accordance with the invention and is comprised of a relatively open fibre structure of relatively low density and contains 0–10% superabsorbent material. The superabsorbent material in the aquisition layer 14 will preferably have a high gel strength, so that an open three-dimensional fibre structure will be retained in this layer after becoming wet. A suitable density range for the aquisition layer 14 is 0.20–0.80 g/cm3. A suitable weight per unit area range for the aquisition layer 14 is 50–1200 g/m2.

The main purpose of the wicking layer 15 is to transport the fluid received in the aquisition layer 14 effectively to the storage layer 16 located beneath the wicking layer 15 and to ensure that the greatest possible part of the storage layer 16 is utilized for absorption purposes. The wicking layer 15 therefore has a relatively low superabsorbent content. A suitable superabsorbent content in the case of the wicking layer 15 is 0–20%, while a suitable density range is 0.25–1.0 g/cm3. A suitable weight per unit area range in the case of the wicking layer 15 is 50–1500 g/m2.

The purpose of the storage layer 16 is to absorb and bind the fluid which is dispersed to the storage layer 16 through the wicking layer 15. The storage layer 16 may therefore have a relatively high superabsorbent content and a relatively high density. Suitable density values are 0.25–1.0 g/cm3, while a suitable superabsorbent content is 40–70%. A suitable per unit area weight range in the case of the storage layer 16 is 100–1500 g/m2.

The wicking layer 15 and the storage layer 16 may optionally be combined to form a single layer. In this case, the single layer will have a relatively high superabsorbent content and a relatively high density. Suitable density values are 0.25–1.0 g/cm3, while a suitable superabsorbent content is 20–70%. A suitable weight per unit area range in the case of a combined wicking and storage layer is 100–2000 g/m2.

When the wicking layer 15 and the storage layer 16 are combined in a single layer, the superabsorbent content of the layer can be varied throughout the product, so as to obtain a superabsorbent gradient in the depth, length and/or the breadth direction of the product.

The various layers may have different forms and sizes. Normally, the absorbent structure is combined with some form of elastication, inter alia in the crotch region of the product, in order to improve product efficiency.

Description of a Second Exemplifying Embodiment

Figure 11:
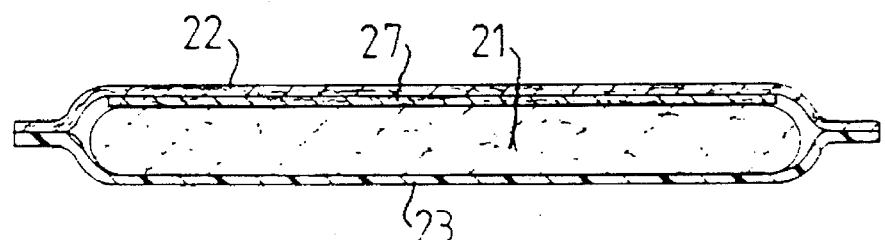

FIG. 11 illustrates an exemplifying embodiment of an inventive sanitary napkin. The napkin comprises, in a conventional manner, an absorbent body 21 which is enclosed between a fluid-permeable top sheet 22, which is suitably composed of perforated plastic film or like material and which lies proximal to the wearer in use, and a fluid-impermeable bottom sheet 23. A thin fluid-permeable layer 27, for instance of non-woven material, may be placed between the absorbent body 21 and the top sheet 22. The sheets 22 and 23 have parts which protrude beyond the absorbent body 21 and the sheets are mutually joined at these protruding parts. The bottom sheet 23 is composed of a suitable plastic material, for instance polyethylene. It will be understood, however, that other known materials may be used for the top and the bottom sheets within the scope of the invention.

The absorbent body 21 is comprised of one single layer. This layer may consist of a dry-formed material according to the invention which contains from 0–10% superabsorbent material. A suitable density range in the case of the absorbent body 21 is 0.6–0.9 g/cm3, while a suitable weight per unit area is 200–300 g/m2. When the absorbent body is composed of a CTMP-material or some other material having a yellowish or brownish colour, a covering layer of chemical pulp white in colour may be applied to the top of the absorbent body.

Description of a Third Exemplifying Embodiment

Figure 12:
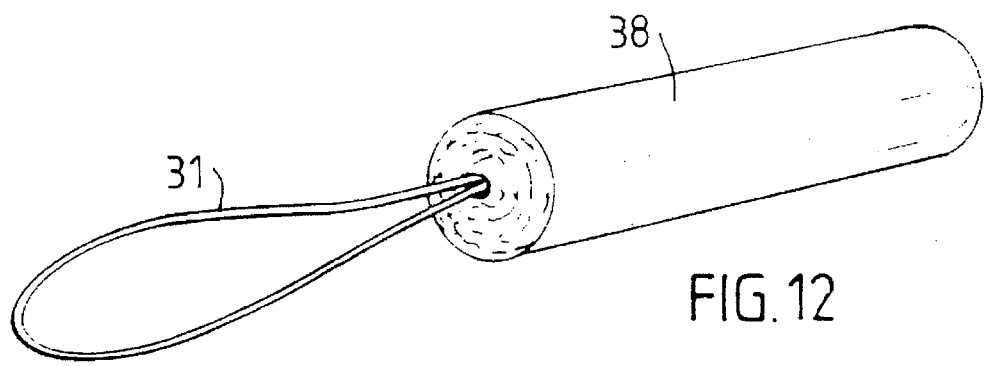

FIG. 12 illustrates an exemplifying embodiment of an inventive tampon. The tampon is comprised of an inventive absorbent material which has been rolled to a cylinder-like form 31. In conjunction with rolling the absorbent material into its cylindrical shape, a string 38 is placed in the centre of the cylinder 31, in a conventional manner, and the cylinder 31 is compressed to the desired thickness and shape, in a conventional manner. Prior to being compressed and shaped, the absorbent material will suitably have a density range of 0.4–0.9 g/cm3 and a weight per unit area of 200–600 g/m2.

Description of a Fourth Exemplifying Embodiment

Figure 13:
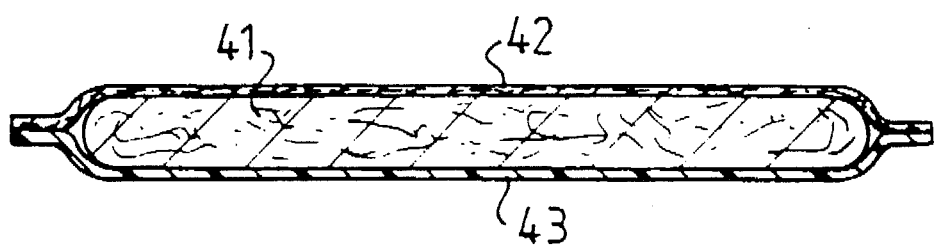

FIG. 13 illustrates an exemplifying embodiment of an inventive wound or sore dressing. The dressing includes, in a conventional manner, an absorbent body 41 which is enclosed between a fluid-permeable top sheet 42, which is suitably comprised of a soft non-woven material, a perforated plastic film or the like, and which is intended to lie proximal to the wearer in use, and a fluid-repellent bottom sheet 43. The sheets 42 and 43 have parts which protrude beyond the absorbent body 41 and are joined together at these protruding parts. The bottom sheet 43 is comprised of a suitable fluid-repellent material, for instance a non-woven material that has been made hydrophobic. It will be understood, however, that the top and bottom sheets may comprise other known materials, within the scope of the invention.

The absorbent body 41 is comprised of only one single layer. This layer may consist of inventive dry-formed material and may be constructed with a relatively open fibre structure of relatively low density and with a superabsorbent content of 0–10%. A suitable density range in respect of the absorbent body 41 is 0.20–0.50 g/cm3 and a suitable weight per unit area is 200–700 g/m2.

Description of a Fifth Exemplifying Embodiment

Figure 14:
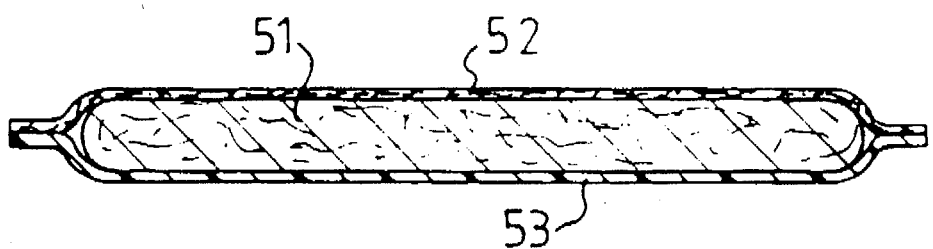

FIG. 14 illustrates an exemplifying embodiment of an inventive saliva absorbent. The saliva absorbent includes, in a conventional manner, an absorbent body 51 which is enclosed between a fluid-permeable top sheet 52, which is suitably comprised of a perforated plastic film or like material and which is intended to lie proximal to the wearer when used, and a fluid-impermeable bottom sheet 53. The bottom sheet 53 is comprised of a suitable plastic material, for instance polyethylene. It will be understood, however, that the top sheet 52 and the bottom sheet 53 may be comprised of other known materials within the scope of the invention.

The absorbent body 51 is comprised solely of one single layer. This layer may be comprised of inventive dry-formed material and has a relatively high density and a superabsorbent content of 20–70%. A suitable density range in respect of the absorbent body 51 is 0.40–0.80 g/cm3.

It will be understood that the invention is not restricted to the illustrated and described exemplifying embodiments thereof and that other embodiments are conceivable within the scope of the following claims.

I claim:

1. A method of producing an absorbent structure in an absorbent article, comprising the steps of:

compressing an air-laid web of cellulose fibres into a dry-formed sheet having a first density of between 0.2–1.0 g/cm$^3$, and mechanically softening said compressed sheet by a non-cutting method to a second density, which is lower than said first density, whereby said sheet is delaminated so as to form a plurality of partially separated thin fibre layers, each of which layers exhibits a density which corresponds to said first density.

2. The method of producing an absorbent structure according to claim 1, comprising softening said dry formed sheet by bending said sheet over one or several edges.

3. The method of producing an absorbent structure according to claim 1, comprising softening said dry formed sheet by bending said sheet over one or several rollers.

4. The method of producing an absorbent structure according to claim 1, comprising softening said dry formed sheet by working said sheet between rollers with engraved patterns.

5. The method of claim 1, wherein the absorbent article is a diaper, sanitary napkin, panty protector, incontinence guard, bed protector, wound or sore dressing, saliva absorbent and like articles.

6. An absorbent structure in an absorbent article, the structure comprising:

5–100% cellulose fibre and also a plurality of thin, partially separated fibre layers and having been produced in accordance with the method of claim 1;

the structure, after having been softened, exhibiting a density reduction of up to and including 75% and a weight per unit area of between 30–2000 g/m$^2$; and each of said thin, partially separated fibre layers exhibiting a density of between 0.2–1.0 g/cm$^3$.

7. The absorbent structure according to claim 6, wherein said first density is between 0.25–0.9 g/cm$^3$.

8. The absorbent structure according to claim 6, wherein said density reduction after softening is up to and including 50%.

9. The absorbent structure according to claim 6, wherein said weight per unit area is between 50–1500 g/m$^2$.

10. The absorbent structure according to claim 6, wherein said cellulose fibres are mainly comprised of flash-dried cellulose fibres.

11. The absorbent structure according to claim 6, wherein said cellulose fibres are comprised mainly of fibres of chemi-thermomechanically produced pulp.

12. The absorbent structure according to claim 11, wherein said chemi-thermomechanical pulp fibres have a curl value of between 0.20 and 0.40.

13. The absorbent structure according to claim 6, wherein said cellulose fibres are comprised mainly of fibres of chemically produced pulp.

14. The absorbent structure according to claim 6, wherein at least a portion of said fibres are chemically stiffened cellulose fibres.

15. The absorbent structure according to claim 6, wherein the structure contains between 0.5–70% superabsorbent material, calculated on the total weight of the structure in a dry state.

16. The absorbent structure according to claim 6, wherein the structure includes reinforcing means.

17. The absorbent structure according to claim 16, wherein the reinforcing means include a binding agent, reinforcing fibre, or thermoplastic binding fibres.

18. The absorbent structure according to claim 6, wherein the absorbent article is a diaper, sanitary napkin, panty protector, incontinence guard, bed protector, wound or sore dressing, saliva absorbent and like articles.

19. An absorbent article, comprising a fluid-permeable top sheet, an essentially fluid-impermeable bottom sheet, and an absorbent body arranged between said sheets, said absorbent body including an absorbent structure according to claim 6.

20. An absorbent article intended for the absorption of blood, such as a tampon or like article, comprising an absorbent structure according to claim 6 mainly comprised of fibres of chemi-thermomechanically produced pulp and including between 0–15% superabsorbent material, calculated on the total weight of the structure in a dry state.

21. The absorbent article according to claim 19, wherein said absorbent body includes at least two layers, an acquisition layer and a second layer, said acquisition layer including means for rapidly taking up fluid and dispersing said fluid to said second layer, said acquisition layer being comprised of a dry-formed sheet containing cellulose fibres and having a first density of between 0.2–0.80 g/cm$^3$ and a weight per unit area of between 50–1500 g/m$^2$ and including a plurality of thin, partially separated fibre layers, wherein said second layer is one of a wicking layer and a storage layer.

22. The absorbent article according to claim 21, wherein said absorbent structure is covered with a layer of chemical pulp on one side thereof.

23. The absorbent article according to claim 19, wherein said absorbent body includes two layers, an acquisition layer and a wicking layer, said acquisition layer including means for rapidly taking up fluid and dispersing the fluid to said wicking layer, said wicking layer being comprised of a dry-formed sheet containing cellulose fibres and having a first density of between 0.25–1.0 g/cm$^3$ and a weight per unit area of between 50–1500 g/m$^2$, and further including a plurality of thin, partially separated fibre layers.

24. The absorbent article according to claim 23, further comprising a storage layer.

25. The absorbent article according to claim 23, wherein said wicking layer includes between 0–40% superabsorbent material.

26. The absorbent article according to claim 19, wherein said absorbent body comprises three layers, an acquisition layer, a wicking layer, and a storage layer, said acquisition layer including means for rapidly taking up fluid and dispersing the fluid to said wicking layer for further transportation to said storage layer, said storage layer being comprised of a dry-formed sheet which contains cellulose fibres and which has a first density of between 0.25–1.0 g/cm$^3$ and a weight per unit area of between 50–1500 g/m$^2$, and further including a plurality of thin, partially separated fibre layers.

27. The absorbent article according to claim 26, wherein said storage layer includes between 20–70% superabsorbent material.

28. The absorbent article according to claim 19, intended for the absorption of blood, such as a sanitary napkin, panty protector or wound or sore dressing, wherein said absorbent structure mainly includes fibres of chemi-thermomechanically produced pulp; and wherein said absorbent structure further includes between 0–15% superabsorbent material, calculated on the total dry weight of the structure.

29. The absorbent article according to claim 28, wherein one side of said absorbent structure is covered with a layer of chemical pulp.

30. The absorbent article according to claim 19, wherein the absorbent article is a diaper, sanitary napkin, panty protector, incontinence guard, bed protector, wound or sore dressing, saliva absorbent and like articles.

* * * * *